United States Patent [19]

Celebuski

[11] Patent Number: 5,858,650
[45] Date of Patent: Jan. 12, 1999

[54] METHODS FOR INACTIVATING NUCLEOTIDE SEQUENCES AND METAL CHELATES FOR USE THEREIN

[75] Inventor: Joseph E. Celebuski, Gurnee, Ill.

[73] Assignee: Abbott Laboratories, Abbott Park, Ill.

[21] Appl. No.: 863,622

[22] Filed: Apr. 3, 1992

[51] Int. Cl.[6] .............................. C12Q 1/68; C12P 19/34; C07H 2/04; C07D 221/02
[52] U.S. Cl. .............................. 435/6; 435/91.2; 435/810; 536/23.1; 536/28.1; 546/1; 546/4; 546/10; 546/26; 546/88; 935/77; 935/78
[58] Field of Search .............................. 435/6, 91, 91.2, 435/810; 935/77, 78; 536/27, 18.7, 22.1, 23.1, 28.1; 546/1, 4, 10, 26, 88

[56] References Cited

FOREIGN PATENT DOCUMENTS 0357011  3/1990  European Pat. Off. .

OTHER PUBLICATIONS

Karn et al. Nature (1966) 211: 160–162.

Thederahn et al J. Am Chem Soc (1989) 111: 4941–4945.

Yamamoto, K. J. Biol Chem (1989) 264: 15435–15440.

Furrer et al. Nature (1990) 346: 324.

*Primary Examiner*—Carla J. Myers
*Attorney, Agent, or Firm*—Wean King Wong; Thomas D. Brainard

[57] ABSTRACT

This invention relates to methods, reagents, and kits utilizing metal chelates to inactivate nucleotide sequences, especially to inactivate polymerase chain reaction (PCR) and ligase chain reaction (LCR) products and to inactivate nucleotide sequences in a bioprocess and bioproduct. A novel metal chelate class is also disclosed.

33 Claims, 2 Drawing Sheets

```
          10        20        30        40        50
     *  *  *  *  *  *  *  *  *  *  *
     GCCAGCCCCCTGATGGGGGCGACACTCCACCATGAATCACTCCCCTGTGAGGAACTACT
     CGGTCGGGGGACTACCCCGCTGTGAGGTGGTACTTAGTGAGGGGACACTCCTTGATGA

---------JHC93---------->
                         -------36/22S---------->
                   ----------5PUT2-S------------>

60       70       80       90       100       110       120
     *  *  *  *  *  *  *  *  *  *  *  *  *
     GTCTTCACGCAGAAAGCGTCTAGCCATGGCGTTAGTATGAGTGTCGTGCAGCCTCCAGGACCCCCC
     CAGAAGTGCGTCTTTCGCAGATCGGTACCGCAATCATACTCACAGCACGTCGGAGGTCCTGGGGGG

------63/19S------->

130      140      150      160      170      180
     *  *  *  *  *  *  *  *  *  *  *  *
     CTCCCGGGAGAGCCATAGTGGTCTGCGGAACCGGTGAGTACACCGGAATTGCCAGGACGA
     GAGGGCCCTCTCGGTATCACCAGACGCCTTGGCCACTCATGTGGCCTTAACGGTCCTGCT 190      200      210      220      230      240      250
     *  *  *  *  *  *  *  *  *  *  *  *  *
     CCGGGTCCTTTCTTGGATCAACCCGCTCAATGCCTGGAGATTTGGGCGTGCCCCCGCAAGACTGC
     GGCCCAGGAAAGAACCTAGTTGGGCGAGTTACGGACCTCTAAACCCGCACGGGGGCGTTCTGACG

<------5PUT1-A--------  <-
                                  <-----------JHC52-----------

260      270      280      290      300      310
     *  *  *  *  *  *  *  *  *  *  *  *
     TAGCCGAGTAGTGTTGGGTCGCGAAAGGCCTTGTGGTACTGCCTGATAGGGTGCTTGCGA
     ATCGGCTCATCACAACCCAGCGCTTTCCGGAACACCATGACGGACTATCCCACGAACGCT

-------JHC51-------        <------299/21A--------
          <-----276/19A-------  <-----299/19A-------
                                         <-----315/18A-

320      330      340       350
     *  *  *  *  *  *  *  *  *
     GTGCCCCGGGAGGTCTCGTAGACCGTGCACC ATG AGC ACG
     CACGGGGCCCTCCAGAGCATCTGGCACGTGG TAC TCG TGC
                                      Met Ser Thr>

METHODS FOR INACTIVATING NUCLEOTIDE SEQUENCES AND METAL CHELATES FOR USE THEREIN

FIELD OF THE INVENTION

This invention relates to the inactivation of nucleotide sequences, more particularly, it relates to the inactivation of nucleic acid products of polymerase chain reaction (PCR) and ligase chain reaction (LCR); and the inactivation of contaminating nucleic acid sequences in a bioproduct or bioprocess.

BACKGROUND

Polymerase chain reaction (PCR) and ligase chain reaction (LCR) are techniques for amplifying any desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to geometrically increase the number of target sequence molecules. PCR is disclosed in U.S. Pat. Nos. 4,683,195 and 4,683,202.

LCR is an alternate mechanism for target amplification. In LCR, two sense (first and second) probes and two antisense (third and fourth) probes are employed in excess over the target. The first probe hybridizes to a first segment of the target strand and the second probe hybridizes to a second segment of the target strand, the first and second segments being positioned so that the primary probes can be ligated into a fused product. Further, a third (secondary) probe can hybridize to a portion of the first probe and a fourth (secondary) probe can hybridize to a portion of the second probe in a similar ligatable fashion. If the target is initially double stranded, the secondary probes will also hybridize to the target complement in the first instance. Once the fused strand of sense and antisense probes are separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described in EP-A-320,308, hereby incorporated by reference. Other aspects of LCR technique are disclosed in EP-A-439,182, to Backman, K. C. et al., hereby incorporated by reference.

Ironically, the biggest virtue of PCR and LCR techniques also poses a significant problem for diagnostic assays. Since both techniques exponentially amplify their targets, they are so sensitive to tiny amounts of target DNA that even ten molecules of oligonucleotide that arise from exogenous sources rather than from the sample itself can lead to a false positive result and mistyping. In the case of PCR, it has been found that if one round of PCR with 25–40 cycles is performed in a volume of 25 $\mu L$, approximately 10,000 contaminating molecules are sufficient to produce a spurious band that can be detected with ethidium bromide. Sarkar, G. et al., *BioTechniques*, 10(5): 591–593 (1991). If nested PCR or booster PCR are used for applications in which DNA from 1–10,000 cells is the input, extreme caution is required because contamination with only one molecule may produce a spurious result. Id.

A primary source of exogenous templates leading to false positive amplifications are carryover products from previous PCR or LCR amplifications of the same target ("PCR products" or "LCR products" respectively) which become dispersed in the laboratory area and serve as templates in subsequent PCR or LCR amplification. PCR or LCR products may also contaminate physically proximate negative samples ("crossover contamination"). Besides contamination by PCR or LCR products, the reagents, samples, equipment, and the general laboratory area may also be contaminated by exogenous DNAs such as bacterial or viral DNAs. For example, PCR may register high levels of background amplification for samples containing water but no DNA, due to the presence of small fragments of DNA which may be produced by autoclaving viral culture material. Porter-Jordan, K. et al., *J. Med. Virol.*, 30(2): 85–91 (1990). RNA contamination is a lesser problem because RNAases are commonly present in the environment. To avoid contamination in the case of PCR, it has been suggested that before adding template DNA and Taq DNA polymerase, individual reaction mixtures should be treated with DNaseI or restriction endonucleases that cut internal to the pair of amplification primers. Furrer, B. et al., *Nature* (London), 346: 6282–324 (1990). This treatment will inactivate contaminating nucleic acid sequences, e.g., render them biologically inactive to polymerase or ligase.

Certain other simple steps are used in PCR to avoid all the above contaminations. They include: (1) physically isolating PCR preparations and products; (2) autoclaving solutions where possible; (3) dividing reagents into aliquots to minimize the number of repeated samplings necessary; (4) using of disposable gloves; (5) avoiding splashes; (6) using disposable replacement pipettes; (7) "premixing" reagents where possible; (8) adding DNA last; and (9) choosing positive and negative controls carefully. Kwok S., et al, *Nature*, 339, 6221, 237–38 (1989).

Additionally, several more specific methods have been described to eliminate carryover DNA target products. These methods include ultraviolet (UV) irradiation (e.g., Amino, et al. *Nature*, 345: 773 (1990), gamma irradiation (Deragan, et al., *Nucl. Acids Res.*, 18: 6149 (1990)), psoralen treatment (Jinno, et al., *Nucl. Acids Res.*, 18: 6739 (1990)), and the use of uracil-N-glycosylase treatment of dU-containing DNA (Longo, et al., *Gene*, 93: 125 (1990); Package Insert, Gene-Amp PCR Carry-Over Prevention Kit, Perkin-Elmer, 1990). UV or gamma irradiation or psoralen treatment in conjunction with UV irradiation is of limited efficiency. The efficiency of such sterilization is dependent on the size and specific sequence of the product. In the case of UV irradiation, for example, longer PCR products (more than 700 base pairs) appear to be more susceptible to UV irradiation than do shorter PCR products (less than 250 base pairs) (Amino, et al., supra.). Additionally, insufficient data have been generated regarding irradiation effect on the chemical integrity of the primers.

In PCR, the carryover contamination problem is solved to some extent, by replacing normal ribonucleoside triphosphates (rNTPs) or deoxyribonucleotide triphosphates (dNTPs) with an exogenous nucleotide that is not present in natural nucleic acid. (See European Patent Application publication no. 0401037, published Dec. 5, 1990, to Hartley). The exo-sample nucleotides used are uracil N-glycosylase (UNG) and uridine triphosphate. The method works thus: the UNG cleaves the glycosidic bond between the base uracil and the sugar deoxyribose, but only when the 2'-deoxyuridine moiety is incorporated into the deoxyribonucleic acid (DNA). The enzyme does not act upon dUTP, free deoxyuridine, or RNA. Thus, if DNA containing 2'-deoxyuridine is introduced into a sample, the adventitious DNA will be cleaved if UNG is present in the medium, while the UNG will not affect the natural DNA. The cleaved DNA will not be a substrate for PCR. In the first cycle of PCR, the UNG will be denatured, and so will not act on the UTP which is incorporated into the growing oligonucleotide chain as part of PCR. Importantly, this method does not address the problem of carryover contamination from native DNA which has the base thymidine instead of uridine, as thymidine is not a substrate for UNG.

Apart from the above PCR investigation, researchers in the field of gene activity and inactivation in live cells also work with the cleavage of DNA. However, since a gene function can be destroyed or altered through even a single cleavage in the nucleotide sequence, the emphasis in this field, site directed mutagenesis, is just to cleave or nick a DNA sequence, preferably at a specific site, in order to observe the resulting effect on the gene function or cell behavior. Thus, the intent is not to totally destroy or inactivate all the DNA sequences, unlike that of PCR or LCR.

Metal chelate complexes have been used in conjunction with oxidizing and reducing agents to damage DNA. The art is replete with findings that reducing agents are required for DNA damage, if metal chelates are used to cleave the DNA. For example, Que et al indicate that the degradation of *Escherichia coli* DNA by 1,10-phenanthroline requires Cu(II), oxygen, and a reducing agent. Que, B. G. et al., *Biochem.*, 19(26): 5987–5991 (1980).

Similarly, Sigman (*Acc. Chem. Res.,* 19: 180–186, 1986) and Goldstein et al. (*J. Am. Chem. Soc.,* 108: 2244–2250 (1986); *J. Free Radicals in Biology & Medicine,* 2: 3–11, 1986) disclose the use of a reducing agent, copper bis(1,10-phenanthroline), and hydrogen peroxide to cleave DNA.

Apart from interfering with LCR and PCR results, undesirable nucleotide sequences also pose a problem in bioprocesses and the resulting bioproducts, for example, in cell-culture-derived recombinant proteins. These contaminating nucleotides can be of viral, fungal, or bacterial origins, such as endogenous and adventitious retroviruses. Knight, P., *Bio/Tech.,* 6(12): 1373-73 (1988). These contaminating nucleotides are health hazards especially if the bioproducts are used in vivo. For example, viral DNA can potentially infect the recipient of a transfused recombinant protein.

The current modes of DNA removal consist of DNAse treatment, polymin P precipitation and anion exchange liquid chromatography separation. The major problem with DNAse treatment is that inhibitors present in the medium can block or slow action of the enzyme. Further, if active DNAase is still present in the recombinant protein preparation that is introduced into a patient, it would seriously jeopardize the patient's health as the DNAase would permeate the patient's cells and destroy the DNA therein. The shortcoming of polymin P precipitation is that it can remove some, but not all, of the endogenous DNA. Finally, anion exchange liquid chromatography carries with it the possibilities of incomplete separation of highly charged protein from DNA, and carryover of sample.

SUMMARY OF THE INVENTION

One aspect of the invention presents methods for inactivating nucleotide sequences in a sample. These methods are preferably applied to inactivate PCR or LCR products, or to inactivate contaminating nucleotide sequences in a bioprocess or bioproduct.

The methods consist of exposing the sample to a metal chelate complex, a reducing agent and an oxidizing agent. The preferred method does not utilize the reducing agent. The preferred two classes of metal chelate complexes are:

(1) Pyridine derivatives of the following chemical formulae (hereinafter referred to as "Class 1 pyridine derivatives"):

wherein "M" denotes the metal. The counterions to the above chelating agent can be determined by those skilled in the art;

and (2) Class 2 metal chelate complexes from the general class of phenanthrolines and their derivatives with the following chemical formulae, X can be Cl, Br, NO$_2$, phenyl, methyl, amidoacetyl, amidoglycyl, and hydrogen. X is preferably hydrogen. L is a donor ligand, preferably a Lewis base such as water and amine. Examples of this class of metal chelate complexes are desferal phenanthroline, substituted phenanthroline, such as Cu (1,10-phenanthroline)$_2$ i.e. copper bis(1,10-phenanthroline).

The metals in both the above two classes of metal chelate complexes are preferably transition metals such as nickel, copper, iron, zinc, ruthenium, rhodium, and cobalt.

Another aspect of the invention presents a class of novel metal chelating agents, Class 1 pyridine derivatives, and their metal chelate complexes as shown above.

Another aspect of the invention presents compositions and reaction mixtures useful for inactivating nucleotide sequences, comprising the above metal chelate complexes, oxidizing agents, and reducing agents. Preferably, no reducing agent is present in the compositions or reaction mixtures.

Another aspect of the invention presents kits for inactivating nucleotide sequences consisting of separate containers with the above metal chelate complexes, oxidizing agents, and reducing agents. Preferably, the kits do not contain reducing agents.

DESCRIPTION OF THE INVENTION

Methods for Inactivating Nucleotide Sequences Using Metal Chelate Complexes

The present invention presents methods utilizing metal chelate complexes for cleaving nucleotide sequences and thus rendering them inactive. This invention can be used in any situation in which exogenous or undesirable nucleotide sequences are to be inactivated. For example, it solves the problem of carryover or crossover DNA contamination by inactivating amplified target DNA, i.e. LCR or PCR products in the case in which PCR or LCR is used. It is understood that the method is not limited to the use in conjunction with PCR or LCR techniques and products, but would be applicable to any technique which amplifies nucleotide sequences and thus would be susceptible to contamination of subsequent samples by the resulting amplified nucleotide sequences. Thus, this inactivation method is preferably used after the amplified target nucleotide sequences have been assayed or detected. Prior to a PCR or LCR reaction, the methods may also be applied to the laboratory area in order to inactivate exogenous nucleotide sequences, especially DNA.

The methods can also be used to inactivate contaminating nucleotides found in a bioprocess or bioproduct. The bioproduct can be a recombinant protein preparation and the bioprocess can be the process by which the recombinant protein preparation is obtained. The bioprocess can include growth, harvest, and purification of the recombinant protein from a recombinant cell culture which produces the recombinant protein. The recombinant cell culture can be a recombinant viral, insect, bacterial, or mammalian cell culture. The cell culture can also be a hybridoma or trioma cell culture, such as those commonly used for the production of recombinant proteins such as antibodies. The recombinant protein includes any protein that can be produced recombinantly. The present invention can be used, for example, to inactivate contaminating viral, bacterial, or fungal nucleic acids that are present in a preparation of recombinant protein.

Nucleotide sequences, such as DNA, exhibit conformational variability that is dependent on the base composition of the nucleotide sequences and the environment. The present invention is applicable to all the conformations which include: single, double, triple stranded DNA or ribonucleic acid (RNA); combinations of DNA and RNA, e.g. DNA-RNA duplex; and linear, closed circular, and supercoiled DNA and RNA.

Due to the sensitivity of the PCR or LCR technology, it is crucial to maximize the inactivation of the PCR or LCR products. The ideal level of inactivation would be the reduction of the amount of viable nucleotide sequences in a sample to a level at or below the amount of nucleotide sequences present before the PCR or LCR amplification. For example, LCR can amplify a target DNA in a sample by one million fold. Viable DNA means DNA which is hybridizable to its complementary strand at the anneal temperature of the operative enzymatic amplification reaction. For the purpose of LCR, this temperature is about 55°–65° C. Preferably, the methods presented in this invention cleave the nucleotide sequences to fragments of such length that they cannot be rehybridized under the annealing condition of PCR or LCR. When a DNA is cleaved, the temperature at which 50% of the DNA hybridizes to a full-length complementary strand (this temperature is referred to as "Tm") is reduced. The DNA is considered nonviable when the majority of the DNA has been cleaved to a length which gives a Tm lower than the anneal temperature.

The methods presented in this application inactivate at least about 40% of the nucleotide sequences present in a sample; and more preferably at least 98% or 99% of nucleotide sequences present in a sample. At above 99%, the preferable efficiency is at least about 99.99%, the next preferable efficiency is at least about 99.9999% (i.e.10$^6$-fold loss of DNA); the more preferable efficiency is at least about 99.99999% (i.e. 10$^7$-fold loss of DNA); and an even more preferable efficiency is at least about 99.999999% (i.e. 10$^8$-fold loss of viable DNA).

The following examples illustrate the method for converting the above exponential factors of inactivation to percentages, for the purpose of this invention. A 100-fold (10$^2$-fold) inactivation of DNA target means that 1 DNA strand out of 100 starting strands is viable towards amplification. Therefore, 99% (99 out of 100) of the sample has been inactivated. A 10$^7$-fold inactivation of DNA target means that 1 DNA strand out of 10,000,000 starting strands is viable towards amplification. Thus, 99.99999% (9,999,999 out of 10 million) of the sample has been inactivated.

The above hybridization method for detecting inactivation of nucleotide sequences is herein referred to as the "amplification detection method". It is directly proportional to the degree of destruction, i.e. the cleavage, of the target nucleotide sequences into such small fragments such that they are incapable of hybridization and thus amplification under the annealing conditions of PCR or LCR. Inactivation of nucleotide sequences can also be determined by physical means, e. g. by estimating the amount and length of the nucleotide sequences remaining after inactivation. This physical detection method is less sensitive than the amplification detection method with the currently available instruments. An example of the detection by physical methods is shown in Example 8 below.

With its high levels of inactivation, this invention is a major advancement over the prior art. Due to PCR's and LCR's abilities to exponentially amplify contaminating nucleotide sequences, to be of practical utility, an inactivation method must achieve at least $10^5$ to $10^7$-fold inactivation of the PCR or LCR product. The amount of inactivation of a DNA target sample for a given method is directly related to the utility of that inactivation method. For example, PCR and LCR will amplify target DNA concentrations several millionfold. As an illustration, let's assume there are 1000 target DNA strands in a sample, and under a particular set of amplification conditions LCR amplifies that quantity by one millionfold. If an inactivation method is only 99% (100-fold) effective, then the method will leave at least $10^7$ DNA molecules (i.e., $10^9$ DNA molecules in the sample, which includes the amplified target DNA, divided by a 100 fold inactivation) as potential contaminants from the sample alone. If the inactivation method is 99.99999% ($10^7$-fold) effective, it would leave about 100 molecules of target DNA ($10^9$ DNA molecules from the sample, which includes the amplified target DNA, divided by $10^7$-fold inactivation) as potential contaminants. Clearly, 100 contaminant DNA molecules are easier to handle than $10^7$ contaminant DNA molecules.

The above methods cleaves native DNA and RNA, unlike the uracil-N-glycosylase method that is currently promoted by the supplier of PCR equipment (GeneAmp PCR Carry-over Prevention Kit, Perkin-Elmer, Norwalk, Conn.). Moreover, when applicants used the above GeneAmp PCR Carry-over Prevention Kit and applied its procedure, applicants found that the uracil-N-glycosylase method gave only a 100-fold loss of viable DNA.

Figure 1:
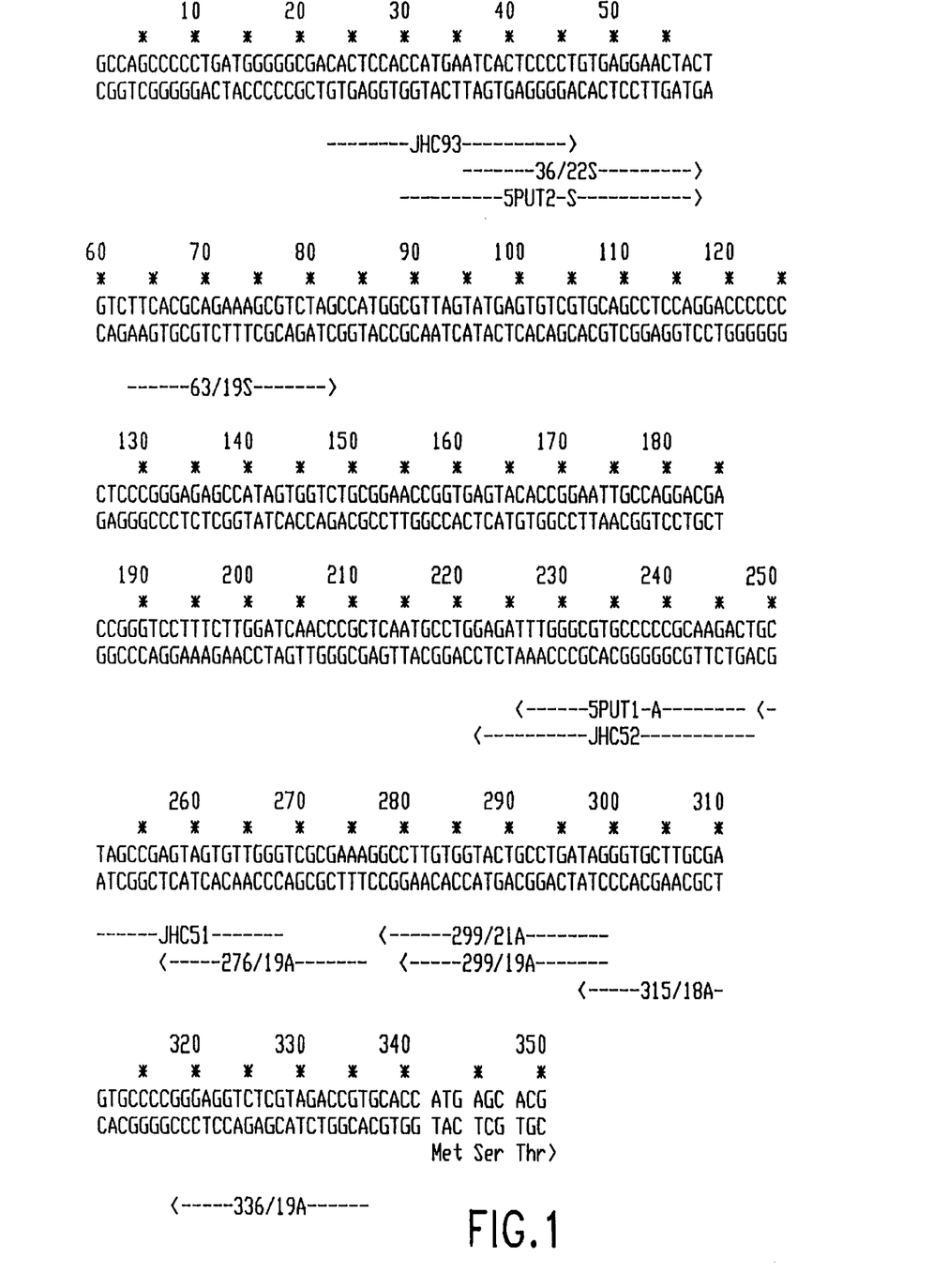
FIG. 1 presents the target and Hepatitis C Virus (HCV) DNA primer sequences used in Example 7.

Applicants' invention preferably cleaves nucleotide sequences into fragments of about 1 to 10 bases in length, more preferably of about 1 to 5 bases in length, and most preferably about 1 to 2 bases in length. Preferably, at least about 99.4% of the nucleotide sequences present in a sample is cleaved into fragments of 1 base in length. The increase in nuclease activity in the current invention is an improvement over the prior art. In the prior art, most of the nucleotides in the sample remained uncleaved, as shown in FIG. 1 of Sigman, *Acc. of Chem. Res.*, supra, at p. 181.

In the case of contaminating nucleic acids in a bioprocess or a bioproduct, such as viral, bacterial, or fungal nucleotide sequences, the main concern is the in vivo biological activities of the contaminating nucleotide sequences in the recipient of the bioproduct. The nucleotide sequences can be inactivated by cleaving them such that they are no longer capable of replicating and/or expressing biological products, such as proteins. To that end, the current invention preferably cleaves the nucleotide sequences to about 1–10 bases in length, more preferably to about 1 to 5 bases in length, even more preferably to about 1 to 2 bases in length, and most preferably to 1 base in length. Alternatively, the degree of cleavage is as indicated in the discussion of the amplification detection method. The level of cleavage just presented would remove most of the contamination, including viral nucleotide sequences which can reach the maximum length of about 10 kilobases.

The methods presented herein uses oxidizing agents and specific classes of metal chelate complexes. Reducing agents may be used in the invention, but are not used in the best embodiment of the invention. The specific classes of metal chelate complexes are Classes 1 and 2 metal chelate complexes shown below. Unlike most prior art, these metal chelate complexes do not cleave only the guanosine base in the nucleotide sequences. Instead, these metal chelate complexes act on positions 1' and 4' of the sugar in the backbone of the nucleotide sequences and are therefore more effective in inactivating the nucleotide sequences and reducing them into smaller fragments.

Contrary to the prior art which requires a reducing agent for maximal efficiency, this invention forgoes the use of a reducing agent in its most preferred embodiment, and surprisingly this, in fact, improves the efficiency of the inactivation of nucleotide sequences. When Examples 5 and 7 are compared, the data shows that copper bis(1,10-phenanthroline) achieved at least 99% inactivation with a reducing agent, and 99.999999% inactivation without a reducing agent. Though copper bis(1,10-phenanthroline) has been used by Sigman, Francois et al., and Goldstein et al., supra, these researchers use reducing agents in their reactions. In fact, Sigman and Goldstein et al., use large amounts of reducing agents.

In applicants' inactivating solution, the final concentration of the metal chelate complex is preferably between about 10 nM to 20 mM; the final concentration of the oxidizing agent is preferably between about 1 $\mu$M to 8M; and if the reducing agent is used, the final concentration of the reducing agent is preferably between about 1 $\mu$M to 8M. More preferably, the metal chelate complex is between about 100 nM to 10 mM, and the oxidizing agent is between about 1 $\mu$M to 8M. The reducing agent preferably has the same ranges as the oxidizing agent.

In the inactivation reaction, for every mole of amplified nucleotide sequence, preferably there are at least 0.18 moles of metal chelate complex, more preferably, between 1.8×$10^{-1}$ to 3.6×$10^5$ moles; and at least 24 moles of oxidizing agent, more preferably, between 2.4×10 to 9.6×$10^7$ moles. More preferably, the respective moles of metal chelate and oxidizing agent are about 1.8×$10^5$ and 2.4×$10^7$. If a reducing agent is used, it would have the same ranges as the oxidizing agent.

Since the metal chelate complex such as copper bis (phenanthroline) sulfate, and oxidizing agent such as hydrogen peroxide are relatively inexpensive, and the amount of the target nucleotide sequence in a sample is unknown and so is the amount of the amplified target, it is preferable to add the inactivating reagents based on the maximum amount of amplified nucleotides expected for the particular amplification technique used, thus insuring maximum inactivation of the amplified target. For example, the expected amounts of amplified molecules of nucleotide sequence in LCR and PCR assay techniques are respectively between $10^{11}$ to $10^{12}$, and $10^{12}$ to $10^{13}$. In the case of LCR, one may take the average of the previous numbers for LCR, i.e. 5×$10^{11}$ molecules of amplified target, as a basis and use between $9 \times 10^{10}$ to $18 \times 10^{16}$ molecules of metal chelate complex, and between $1.2 \times 10^{13}$ to $4.8 \times 10^{19}$ molecules of oxidizing agent. More preferably, $9 \times 10^{16}$ and $1.2 \times 10^{19}$ molecules of metal chelate complex and oxidizing agent, respectively, may be used.

Alternatively, given a sample solution with an unknown amount of nucleotide sequences to be inactivated, one may use the range of concentrations shown above for the inactivating solution, except that the volume on which the molarities of the reagents are calculated would be the sum of the sample solution and the added reagent solution. For example, at a minimum, there should be about 10 nM of the metal chelate in the final solution consisting of the sample solution and the reagent solution.

The oxidizing agents are preferably electrophilic or free radical reagents. Examples of the oxidizing agents are: peroxides in general, such as hydrogen peroxide, oxone ($KHSO_5$), t-butyl hydroperoxide, peracetic acid, and magnesium monoperoxyphthalate (MMPP); persulfates in general, such as sodium persulfate, and ammonium persulfate. The preferred oxidizing agent is hydrogen peroxide.

The reducing agents are preferably nucleophilic agents capable of donating electrons. Examples of the reducing agents are: thiol, ascorbate, NADH, dithiothreitol, mercaptopropionic acid, glutathione, cysteamine and cysteine. The preferred reducing agent is dithiothreitol.

The reaction is preferably carried out in an inert solvent, such as distilled water or a buffer between a pH of about 2 to 13. Examples of the buffers are the LCR buffer described in Example 5 below, BSA buffer described in EP-A-439,182 supra, or Tris pH 8.2. The LCR, BSA, and Tris buffers contain amine. In the case of Class 2 metal chelates, the buffer preferably contains water or amine, which serves as the ligand "L" (shown below under the section "*Metal Chelate Complexes*"). The reaction is preferably carried out at a temperature between about 4° C. and 75° C. More preferably, the reaction is carried out at an ambient temperature.

The most preferred inactivation method uses copper bis (1,10-phenanthroline) and hydrogen peroxide as reagents, and without adding a reducing agent, for inactivating nucleotide sequences. The method is referred to as "copper bis(phenanthroline) sulfate/hydrogen peroxide" method or reaction. The copper bis(1,10-phenanthroline) is preferably in the form of copper bis(1, 10-phenanthroline) sulfate. The copper bis(1,10-phenanthroline) is preferably present in a final concentration of about 15 $\mu$M to 20 mM, and the hydrogen peroxide is preferably present in a final concentration of about 150 mM to 8M by volume (v/v), with the reaction run at ambient temperature in an inert solvent. The inactivation is almost instantaneous. In not requiring a reducing agent in its most preferred embodiment, the present invention reduces the costs, inconvenience, and complications associated with the use of an additional reagent.

The invention also presents a novel class of chelating agents, the Class 1 pyridine derivatives, and their metal chelate complexes. Examples of this class are nickel or copper ethyl perchlorate (the formulae for these compounds are shown in the following section: "*Metal Chelate Complexes*"). These novel metal chelate complexes have surprisingly increased efficiency of DNA inactivation when compared to their closest prior art metal chelate complex counterparts, referred to herein as propyl perchlorate (as shown in Example 6). This advantage is apparent in the comparative data between the two in Example 6 below. Unlike Example 7 which used the amplification detection method, Example 6 only detected whether the metal chelates tested would cleave the DNA. In Example 6, a single cleavage on the DNA strand was sufficient to prevent its detection by the IMx® MEIA assay. Example 6 shows that the nickel ethyl perchlorate is 42% efficient in inactivating the nucleotides, as compared to the dismal performance of nickel propyl perchlorate (6%).

In the case of inactivating PCR or LCR products, after the PCR or LCR experiment has been completed and the assays for target nucleotide sequences have been taken, a mixture of the metal chelate complex, an oxidizing agent, and a reducing agent (preferably no reducing agent is used) are applied to the samples, pipettes, gels or any surface which may have been contacted by the PCR or LCR products or their aerosols.

The method may also be used to decontaminate laboratory area, equipment and reagents before an assay or a bioprocess is conducted in order to remove exogenous nucleotide sequences in the environment, such as microbial DNA contamination.

The following presents an example in which the present invention may be used. When PCR or LCR is used as a diagnostic tool for a DNA target, the samples are placed in a DNA Thermal Cycler (Perkin Elmer, Norwalk, Conn.) with the appropriate reagents to amplify the target DNA that is to be detected. After the completion of the amplification, the samples are transferred to an assay device which would detect the amplified target DNA. An example of the assay device is an IMx® instrument (Abbott Laboratories, Abbott Park, Ill. For descriptions of the instrument, its operation and general protocol, see also, Barnes et al., *J. Clin. Imm.*, 14 (2): 115–119 (1991) and EP-A-288,793; Ludington et al., *Clin. Chem.*, 34(9), 1726–1732 (1988)). At the completion of the assay, the samples would be disposed of. Often, it is at this stage that contamination occurs. This is because generally, the same technician would perform the amplification and assay. When manually disposing the samples at the end of the assay, the technician may spill onto himself/herself the amplified target DNA (PCR or LCR products) from the samples. Alternatively, the PCR or LCR products may be found in the air as aerosol and attached to the technician's person, gloves or garment. Thus, he/she may contaminate the new samples with the LCR or PCR products, when the technician returns to handle the new samples and operate the Thermal Cycler. The contaminating LCR or PCR products are thereby inadvertently amplified in the new samples and thereby cause inaccurate assay result, e.g. false positive results. In view of the above, it would be useful to inactivate the LCR or PCR products after the samples have been assayed and before they are handled by the technician for disposal, to prevent them from contaminating the technician and thus the new samples. The inactivation may be achieved by dispensing the inactivating reagents disclosed herein of metal chelate complexes, together with an oxidizing agent and a reducing agent (preferably without the reducing agent), into the assayed samples, and allowing an appropriate time for the inactivation to occur (in most cases, the reaction would be almost instantaneous at ambient temperature), before handling and disposing of the assayed samples. Preferably, the assayed samples are sealed off after the inactivation reagents have been dispensed into the assayed samples, and before handling and disposal of the assayed samples.

The above methods and metal chelate complexes can also be used to inactivate contaminating nucleotides in a bioprocess or a preparation of bioproducts. In this case, the inactivating reagents are added during the operation of a bioprocess or to a preparation containing the bioproduct to preferably cleave the contaminating nucleotide sequences so that they are no longer capable of replicating and/or expressing biological products. The bioproduct, such as a protein, can be separated from the inactivating reagents by ultrafiltration, protein precipitation, size exclusion chromatography, dialysis, and/or other protein purification methods. For example, the protein can be dialyzed against 100 mM tris/100 mM NaCl, pH 7.0 in dialysis tubing with a 30000 dalton cutoff (Schleicher and Scheull, Keene, N.H.). Alternatively, the protein can be concentrated using an Amicon (Beverly, Mass.) ultrafiltration device, with a 30,000 dalton cutoff, and the protein is then washed twice with 20 mL to 100 mL tris/100 mM NaCl. Alternatively, the protein can be subjected to size exclusion chromatography using Bio-Rad Bio-Gel P100 (Richmond, Calif.), and eluted with 50 mM tris.

Metal Chelate Complexes

The preferred two classes of metal chelate complexes are: (1) Class 1 pyridine derivatives with the following chemical formulae:

wherein "M" denotes the metal. The metal counterions to the above are preferably monovalent or divalent anions, for example, chloride, bromide, sulfate, tetraflouoroborate, tetraphenylborate, hexafluorophosphate, nitrate, and perchlorate. Preferably, the counterions are sterically rigid and bulky complexes that would aid in the crystalization of the metal chelate complexes for ease of isolation and purification. Examples of the preferred counterions are: perchlorate, tetrafluoroborate, and tetraphenylborate. Examples of the members of this Class 1 pyridine derivatives are nickel and copper ethyl perchlorates of the following formulae:

and (2) Class 2 metal chelate complexes from the general class of 1,10-phenanthrolines with the following chemical formulae, wherein "M" denotes a metal. The metal counterions to the above are preferably monovalent or divalent ions, examples of which are the same as those listed for the Class 1 metal chelate complexes. X can be Cl, Br, $NO_2$, phenyl, methyl, amidoacetyl, amidoglycyl, and hydrogen. X is preferably hydrogen. L is a donor ligand, preferably a Lewis base such as water and amine. Examples of this class of metal chelate complexes are desferal phenanthroline, substituted phenanthroline; and copper (1,10-phenanthroline)$_2$ i.e. copper bis (1,10-phenanthroline).

For both of the above classes of metal chelate complexes, the metal ion is preferably a transition metal ion such as nickel, copper, iron, zinc, ruthenium, rhodium, and cobalt. More preferably, the metal ion is capable of catalyzing oxidation-reduction reaction.

Synthesis of the Metal Chelate Complexes

The metal chelate complexes can be synthesized using methods well-known in the art, such as those disclosed in Karn et al., *Nature*, 211: 160–163 (1966). Complexes of the chelating agent and metal ions may generally be formed by incubation of the chelating agent with the metal ion in a buffered solution in which the two reactants are stable. Suitable buffers include those with weak metal-binding properties, such as citrate, acetate, or glycine. Appropriate concentrations, temperatures and pH may be selected by one skilled in the art to ensure the metal ions bind to the chelating functionality. It is particularly desired that all solutions be free of metal impurities. After incubation for an appropriate period of time, unbound metal ions may be separated, if necessary, from the metal chelate complex by a procedure such as gel filtration or crystallization.

Also presented herein are kits for inactivating nucleotide sequences equipped with containers containing the above metal chelate complexes, oxidizing agents, and reducing agents. Preferably, the kits do not contain reducing agents.

Having described the invention in general, the following Examples present specific embodiments of the invention.

EXAMPLES

For Examples 1 to 6, the oligonucleotides were labeled at the ends with either novel carbazole or novel adamantane derived haptens (described in co-pending U.S. patent application serial number 808,508, filed Dec. 17, 1991, by Mattingly, P. G., entitled "Haptens, Tracers, Immunogens and Antibodies for 3-phenyl-1-adamantaneacetic Acids"; and co-pending U.S. patent application serial number 808,839, filed Dec. 17, 1991 by Fino, J. R., entitled "Haptens, Tracers, Immunogens and Antibodies for Carbazole and Dibenzofuran Derivatives." The method for adding a hapten to the 3'-end of an oligonucleotide is disclosed in co-pending U.S. patent application Ser. No. 630,908, filed Dec. 20, 1990; the method for adding a hapten to the 5' end is through the use of a phosphoramidite reagent is described in Thuong, N. T. et al., *Tet. Letters*, 29(46): 5905–5908 (1988), or Cohen, J. S. et al., U.S. patent application Ser. No. 07/246,688 (NTIS order no. Pat-Appl-7-246,688 (1988) )

Before LCR amplification, one of the sense probes was labeled at its 5' end with carbazole, the other of the sense probes was labeled at its 3' end with adamantane. This is similarly done for the anti-sense probes. LCR was then conducted using these probes and the method disclosed in EP-A-439,182, supra. An alternative method that can be used is disclosed in EP-A-320,308, to Backman, K. C. The amplified and ligated DNA would have a carbazole and a adamantane at either end (hereinafter referred to as "carbazole-nucleotide sequence-adamantane hapten") for detection by the IMx® instrument below.

The quantitative inactivation results of the above labeled oligonucleotides were determined on an IMx® instrument (Abbott Laboratories, Abbott Park, Ill. The components of the reaction cells are shown in FIG. 2(a) of *Clin. Chem.*, 34(9), supra, at 1727) using microparticle enzyme immunoassay (MEIA) technology. The protocol is run similar to that used in the commercially available alpha-fetoprotein assay, with the following adaptions: (1) the anti-alpha-fetoprotein antibody coated microparticles are replaced with anti-carbazole antibody coated microparticles (hereinafter referred to as "anticarbazole coated microparticles"); (2) the conjugates of anti-alpha fetoprotein antibodies: alkaline phosphatase are replaced with the conjugates of anti-3-phenyl-1-adamantaneacetic acid antibodies: alkaline phosphatase (hereinafter referred to as "antiadamantane conjugated to alkaline phosphatase"). The protocol for the IMx® MEIA assays is further described in EP-A-439,182, supra.

In brief, this protocol is as follows. A 100 µL of the sample which has been amplified by LCR is pipetted into the sample well. 30 µL of this sample is then pipetted into the incubation well, the anticarbazole coated microparticles are added to the well. An appropriate period of incubation follows which allows the formation of a complex consisting of anticarbazole and nucleotide sequences with the carbazole ends. After the incubation, the mixture is pipetted onto the glass fiber capture matrix of the IMx® reaction cell, and antiadamantanes conjugated to alkaline phosphatases are added. This leads to a microparticle-oligonucleotide-enzyme complex which will stay on the surface of the glass fiber capture matrix. After the removal of excess reagent in a wash step (throughout this protocol, the blotter beneath the glass fiber capture matrix absorbs reagent solutions which would otherwise overflow the glass fiber capture matrix), the glass fiber capture matrix is treated with 4-methylumbelliferyl phosphate (MUP). The surface-bound enzyme converts the nonfluorogenic MUP to 4-methylumbelliferone (MU), whose fluorescence can be measured. The numerical values given in the following examples are the rate reads of this process, expressed in counts/sec/sec (cpss). The amount of viable DNA is directly related to this rate read, and so inactivation of DNA can be monitored by this technique. A reading of 20 cpss for a sample would indicate that at least about $10^9$ molecules of carbazole-nucleotide sequence-adamantane hapten are present in the sample. This concept of MEIA readout of labeled oligonucleotides is described in European Patent Application, publication No. 357,011, published Mar. 7, 1990, "Detection and Amplification of Target Nucleic Acid Sequences," to Laffler, T. G., et al.

The above amplification detection method are applicable to other amplification techniques. For example, it can be similarly applied to PCR products. The illustrative amplification of haptenated primers in PCR and the MEIA of the resulting PCR products is described in EP-A-357,011 to Laffler, et al.

The reagents copper bis(1,10-phenanthroline) sulfate and iron-EDTA sulfate were prepared by dissolution of stoichiometric quantities of component metal salts with organic ligand in aqueous media. All chemicals were obtained from Aldrich Chemical Co. (Milwaukee, Wis.).

Example 1
Preparation of Nickel Ethyl Perchlorate Chelate Complex

The following describes the preparation of nickel ethyl perchlorate chelate complex of the following formula:

A solution of 1189 mg $NiCl_2(H_2O)_6$ (5 mmol), 816 mg (5 mmol) of 2,6-diacetylpyridine, and 540 µL (5 mmol) of diethylenetriamine in 20 mL of 1:1 water:ethanol was heated in a 70° C. oil bath for three days. The ethanol was carefully removed by rotary evaporation, and 15 g of sodium perchlorate in 10 mL of water was added. After standing for 1 hour at room temperature, the supernatant was decanted off. The residual solids were dissolved into 16 mL of hot distilled water, and gravity filtered through fluted filter paper. The filtrate was left to stand at 4° C. for 4 hours. The supernatant was decanted off, and the orange-red crystals were washed with 2×10 mL cold (4° C.) water, then vacuum dried to give 87.4 mg of product, 3.6% yield. Fast atom bombardment mass spectral analysis showed the expected pattern of isotopic peaks for product.

Example 2
Preparation of Copper Ethyl Perchlorate Chelate Complex

The following describes the preparation of copper ethyl perchlorate chelate complex, a member of the Class 1 pyridine derivatives, of the following formula:

$(ClO_4^-)_2$

To 672.2 mg (5 mmol) of copper chloride and 815.9 mg (5 mmol) of 2,6-diacetylpyridine was added 540 μL (5 mmol) of diethylenetriamine. Immediately, an exothermic reaction ensued, and the green copper chloride turned blue in color. Then, 20 mL of 1:1 ethanol:water was added, and the solution was kept in a 65° C. oil bath for three days. After 15 g of sodium perchlorate in 10 mL of water was added, the ethanol was carefully removed by rotary evaporation. The crude brown solid was filtered off, and was taken up into 10 mL boiling water as much as possible. The solution was gravity filtered through fluted filter paper, and the filtrate left to stand in a 4° C. refrigerator for 24 hours. The supernatant was decanted off, and the blue crystals were manually separated from the amorphous brown solid. The blue crystals were copper ethyl perchlorate chelate complex, at 195.5 mg and 8% yield. Mass spectral analysis showed the M+H peak for the product.

Example 3
Use of Copper Ethyl Perchlorate Chelate Complex to Inactivate DNA

10 μL pooled LCR product was treated with 30 μL of 10 mM hydrogen peroxide, 30 μL of mM dithiothreitol (DTT), and 3 μL of 10 mM copper ethyl chelate complex (of Example 2) at 60° C. for 1 hour. The reaction was tested for loss of viable DNA using the IMx® instrument. The untreated LCR controls had rate reads of 560 cpss, while the treated DNA had rate reads of 325 cpss, indicating a loss of 42% of signal and thus of DNA in the treated DNA solution. Control experiments established that none of the reagents, individually, would attenuate the MEIA signal or inactivate DNA.

Example 4
Preparation of Copper Bis(1,10-phenanthroline) Sulfate

The following describes the preparation of a 10 mM stock solution of Cu(phenanthroline)$_2$SO$_4$. To a 100 mL of distilled water, in an Erlenmeyer flask, was added 162 mg (1.0 mmol) of anhydrous copper sulfate (Aldrich Chemical Company, Inc., Milwaukee, Wis.). The solid immediately caked into pale blue chunks on the bottom of the Erlenmeyer flask. Upon swirling of the Erlenmeyer flask, these pale blue chunks slowly dissolved. To this solution was added 399 mg (2.0 mmol) of 1,10-phenanthroline hydrate (Aldrich Chemical Company, Inc. supra.). At this point, there were needles of phenanthroline floating atop the aqueous suspension. These needles of phenanthroline were dissolved by sonication for 5 minute in a Branson M2200 sonicator. The resulting solution was an aquamarine blue, 10 mM solution of Cu(phenanthroline)$_2$SO$_4$. Using a Beckman DU70 spectrophotometer, the $A_{720}$ of this solution was found to be 0.61 O.D.

Example 5
Use of Copper Bis(phenanthroline)/Hydrogen Peroxide/DTT to Inactivate DNA

To 30 μL of highly positive LCR sample were added 30 μL of 10 mM DTT, 30 μL of 10 mM hydrogen peroxide, 3 μL of 10 mM copper bis(1,10-phenanthroline) sulfate and 36 μL of LCR buffer consisting of: 50 mM [4-(2-hydroxyethyl)-1-piperazinepropane-sulfonic acid] (its abbreviation in the art is EPPS), 30 mM MgCl$_2$, titrated to pH 7.8 in KOH, and 100 mM nicotinamide adenine dinucleotide (its abbreviation in the art is NAD). After heating the reactions at 50° C. for 1 hour, the samples were pipetted into the sample well of the IMx® reaction cell and the MEIA assay run. The positive control (untreated) DNA had a rate read of 727 cpss higher than background, and the copper bis(1, 10-phenanthroline) treated DNA had a rate read of 1.2 cpss higher than background, indicating that the treated DNA sample had a minimal DNA inactivation rate of 99.8%.

Example 6
Comparison of Quantities of DNA Inactivation for Different Metal Chelates on the Same Sample of DNA A pool of adamantane-carbazole labeled LCR product DNA was aliquotted such that a 35 μL sample of the LCR product pool was used for each inactivation reaction. To this 35 μL of solution was added 30 μL of 10 mM DTT, 30 μL of 10 mM hydrogen peroxide, and 30 μL of 10 mM metal chelate in distilled water. The reactions were run at 45° C. for 1 hour.

The chelates used were nickel propyl perchlorate, nickel ethyl perchlorate (of Example 1), copper bis(1,10-phenanthroline) sulfate and iron (EDTA) sulfate.

The nickel propyl perchlorate tested was prepared by the method of Busch and Karn in Nature 211:160–163 (1966) and is of the following formula:

$(ClO_4^-)_2$

The positive (untreated) control gave a rate read of 103 cpss above background. The cpss values above background for metal chelate treated DNA samples were: 97 cpss for the nickel propyl perchlorate, indicating a reduction of 6%; 60 cpss for the nickel ethyl perchlorate, indicating a reduction of 42%; 1.6 cpss for copper bis(1,10-phenanthroline) sulfate, indicating a reduction of 99%; and 80 cpss for iron-EDTA sulfate, indicating a reduction of 22%.

Example 7
Inactivation of DNA Using Copper Bis(1,10-phenanthroline) and Hydrogen Peroxide Only A pool of amplified LCR product was aliquotted such that 75 μL of product pool would be present in each inactivation reaction. Some samples were treated by adding 5 μL of 10 mM copper bis(1,10-phenanthroline) followed by 10 μL of 2M (6.8%) hydrogen peroxide. After 5 minutes at room temperature, the reactions were tested for the presence of viable DNA on the IMx®. The positive control (untreated) samples had rate reads of 833 cpss over background. The copper bis(1,10-phenanthroline) treated samples had rate reads of 1.5 cpss over background, for a minimal reduction of 99.8% of signal. Further LCR amplification on the remainder of the copper treated sample, diluting the sample so that there was no polymerase or ligase inhibition, showed that the metal chelate treatment reduced the amount of viable DNA by a minimum $10^7$-fold, (i.e., the equivalent of inactivating 99.99999% of DNA present in a sample). The number was arrived at by serially diluting the inactivated amplified sample (at a factor of 10-fold) to arrive at the same rate read as that possessed by the amplified sample that was not inactivated.

The above experiment was repeated several times. It was observed that the best efficiency achieved was at least 99.999999% inactivation of the nucleotide sequences (i.e. $10^8$-fold loss of viable DNA). A million-fold loss of viable DNA was seen in the worst result (i.e. 99.9999%). In the experiments to date, the average loss of DNA is about $10^7$-fold.

Example 8
Physical Determination of Nucleotide Sequences Left After Inactivation After the treatment of $1.6 \times 10^{14}$ molecules of 25-mer oligonucleotide with copper bis(phenanthroline) sulfate/hydrogen peroxide (as in Example 7 above), capillary electrophoresis (Beckman P/ACE 2000, Beckman Instruments, Palo Alto, Calif.) analysis of the treated sample showed only nucleotides of one base in length based on UV absorbance at 254 nm. The experiment was carried out as follows.

The crude reaction was injected onto a 37 cm long polyacrylamide capillary. The capillary was thermostated at 30° C., and the voltage was kept constant at 11.1 kV. The UV absorbance of the resolved peaks was recorded by the instrument's onboard computer. Under these conditions, single base nucleotides migrated at 12 min. Full length oligonucleotides migrated at about 20 min.

In previous work, applicants had found the limit of detection of this method for DNA strand is at a minimum $10^{12}$ molecules of DNA. A minimum of $10^{11}$ molecules is the limit of detection for nucleotides of 1 to 2 bases. The above UV absorbance did not indicate the presence of any nucleotides longer than one base. Thus, at least approximately 99.4% of the nucleotides in the sample was of 1 base in length.

Example 9
Inactivation of PCR Template DNA with Copper Bis(1,10-phenanthroline) Sulfate Inactivation of PCR template DNAs by the addition of copper bis(1,10-phenanthroline) sulfate and hydrogen peroxide was demonstrated using the Hepatitis C Virus (HCV) 5'-untranslated region as the target DNA. The PCR primers, designated JHC93 and JHC52, and the target DNA sequence are presented in FIG. 1 and illustrate the expected 226 base pair PCR product spanning HCV nucleotides 23–248. PCR was conducted using the Gene Amp kit (available from Perkin-Elmer, Norwalk, Conn.) and following the manufacturer's recommended procedures. Briefly, 100 μL volume PCR reactions were conducted in the presence or absence of 15 μl of 10 μM copper bis(1,10-phenanthroline) sulfate and 10 μl of 2M hydrogen peroxide using approximately 50 ng or 0.5 ng of HCV 5'-untranslated DNA fragment. The PCR primers JHC 93 and JHC 52 were used at 500 ng per reaction which consisted of thirty cycles of 94° C. for one minute, 50° C. for two minutes, and 72° C. for two minutes. A control PCR reaction lacking DNA template was also run to assess the potential of PCR product contamination in the reagents, equipment, or from the laboratory environment. Twenty microliter aliquots of the PCR reactions were removed and analyzed by agarose gel electrophoresis and the DNA fragments stained with ethidium bromide, according to the method described by Maniatis, et al., (Molecular Cloning, A Laboratory Manual, Cold Spring Harbor Laboratory, 1984).

Figure 2:
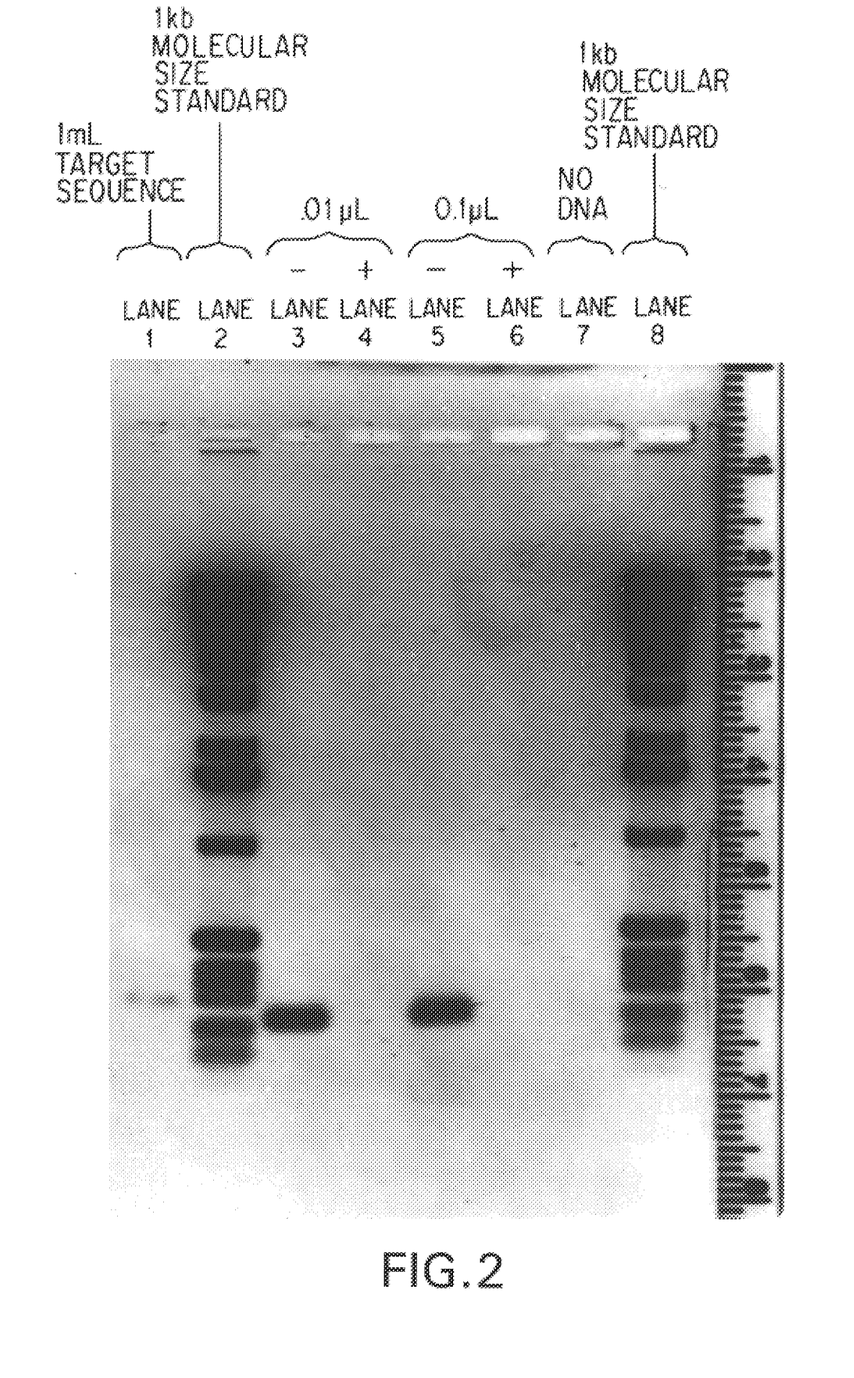
FIG. 2 presents an analysis of the PCR products by agarose gel electrophoresis. Lane 1 contained 1 μL of the target sequence; Lane 2 contained molecular size standard of one kilobase ladder; Lanes 3 and 5 contained 0.01 and 1 μL respectively of PCR products in the absence of copper bis(1,10-phenanthroline) sulfate/hydrogen peroxide; Lanes 4 and 6 contained 0.01 and 1 μL, respectively, of PCR products in the presence of copper bis(1,10-phenanthroline) sulfate/hydrogen peroxide; no DNA has been added to Lane 7; Lane 8 contained molecular size standard of one kilobase ladder.

FIG. 2 presents the results of this analysis where lane 1 contained approximately 50 ng of the HCV 5'-untranslated HCV template DNA, lanes 2 and 8 contained molecular weight standards (1 kb ladder, Catalog No. 5615SA, available from Bethesda Research Laboratories, Gaithersburg, Md.); lanes 3 and 4 contained PCR reactions using 5 ng of template DNA in the absence or presence of copper bis(1,10-phenanthroline) sulfate and hydrogen peroxide, respectively; and lanes 5 and 6 contained PCR reactions using 50 ng of template DNA in the absence or presence, respectively, of copper bis(phenanthroline) sulfate and hydrogen peroxide; and lane 7 contained the PCR reaction conducted in the absence of DNA template. Lanes 3 and 5 clearly demonstrate the 226 bp HCV PCR product expected, while lanes 4 and 6 lack detectable levels of this product. The PCR products were further subjected to Southern blot analysis (Maniatis, et al., supra.) wherein the agarose gel separated DNA fragments are transferred to a nylon membrane, denatured, and hybridized with radioactively labelled DNA probe homologous to the target DNA sequence. The following describes the results of subjecting the gel described in FIG. 2 to Southern blot analysis. Lanes 1, 3, and 5 show strong hybridization signals when exposed to X-ray film, but lanes 4 and 6 do not show any observable signal. This sensitive detection method clearly demonstrates that the addition of copper bis(phenanthroline) sulfate and hydrogen peroxide completely inhibits the ability of PCR to amplify and detect the template DNA. Additionally, lane 7 demonstrates that even in the absence of the desired target template, rather strong hybridization signal is generated by PCR. This type of contamination problem is precisely the problem that this invention seeks to eliminate.

Example 10
Nucleic Acid Decontamination Procedure of Bioproduct Preparation Using Copper Bis(phenanthroline) Sulfate All steps should be conducted at 4° C. unless indicated otherwise. One liter of *Escherichia Coli (E.Coli)* cell culture is centrifuged at 500 g for 15 minutes. The supernatant is decanted and the pellet weighed. All quantities of the reagents cited here are based on 1 gram of wet weight of *E. Coli*. To the pellet is added 3 mL of 50 mM tris-HCl pH 8.0/1 μM EDTA/100 mM NaCl. Then, 8 μL of 50 mM phenylmethylsulfonyl fluoride is added, followed by 80 μL of 10 mg/mL lysozyme. Then, 4 mg of deoxycholic acid is added with continuous stirring. The lysis mixture is then manually stirred at 37° C. with a glass rod. When the lysate becomes viscous, 15 μL of 10 mM aqueous copper bis (phenanthroline) sulfate is added, followed by 10 μL of 2M aqueous hydrogen peroxide. Within 30 minutes at room temperature, the lysate is no longer viscous. After centrifugation to remove cell debris, the crude protein can be purified using standard chromatographic or precipitation techniques.

Example 11

Inactivation of LCR or PCR Products

The following briefly describes how the inactivation of LCR or PCR products can be used in a diagnostic assay. It describes the amplification of the target DNA in a sample solution by means of LCR or PCR; the assay for the target DNA with the aid of an IMx® instrument; and after the IMx® assay reading has been taken, the inactivation of the LCR or PCR amplified target DNA (i.e. LCR or PCR products); and the disposal of the sample solution.

To amplify the target DNA in a sample solution, 100 µL of the sample solution is added to 100 µL of LCR buffer containing thermophilic enzymes, labelled oligonucleotide probes, and co-factors needed for LCR. The reagents and method for conducting LCR are disclosed in EP-A-439,182 supra. The sample solution is contained within silanized Eppendorf tubes with screw caps. The sample tubes are placed in the heating wells of a Perkin-Elmer M9600 thermal cycler (Perkin-Elmer, Norwalk, Conn.), and cycled between 55° C. and 85° C. 40 times, with the temperature held at each set point for 1 minute. PCR may be similarly used in this step by replacing the LCR DNA amplification step with a PCR DNA amplification step, using PCR reagents and procedures known in the art.

To assay for the amplified target DNA in the sample, the sample tubes are removed from the thermal cycler, and placed in the sample well of a reaction cell in an IMx® instrument. The protocol described herein does not utilize the predilution well of the reaction well. The reaction cell is removable from the IMx® instrument and contains a sample well and an incubation well. The IMx® instrument is a self-contained unit with a front panel which can be opened to allow the placing of the sample tubes onto the reaction cells. The front panel is then closed and the assays are conducted automatically. A pipetting arm in the IMx® instrument would pierce the cap on the Eppendorf tubes, and dispense the amplified target DNA product (i.e. LCR or PCR products) into the appropriate reaction wells in the reaction cell to which re-agents for detecting the target DNA are added. The pipette transfers the reaction mixture to the glass fiber capture matrix, here the reaction between the LCR or PCR products and the reagents would produce a fluorescent signal which is read by the IMx® instrument and the test results are tabulated by an instrument on board the IMx® instrument.

After the completion of each pipetting, the pipet is automatically washed twice. The commercially available IMx® instrument contains features for the automatic washing of the pipette using line diluent buffer. Briefly, the pipette is placed in a container containing the line diluent buffer and the buffer is drawn into the pipette. Then the pipette expels the buffer into another container. This procedure is repeated a second time to clean the pipette.

The amount of cross-contamination of the PCR or LCR between neighboring samples during the assay run is negligible for the purpose of the assay results. The cross-contamination is only significant if the PCR or LCR products contaminate a sample which is later amplified before it assayed, thereby increasing the contamination exponentially and giving a false reading.

After the test results have been taken, the LCR or PCR products are then inactivated. The inactivation step is conducted automatically by the IMx®instrument. The pipetting arm adds 15 µL of 10 mM copper bis(1,10-phenanthroline) sulfate and 10 µL of 2M hydrogen peroxide to each incubation well and Eppendorf tube. Some of this inactivation reagent mixture may aerosolize and be dispersed within the IMx® instrument, along the manner of the aerosolization and dispersement of the nucleotide sequences in the sample during the assay run. This dispersed reagent mixture can then inactivate the nucleotide sequences that has aerosolized and dispersed within the IMx® instrument. The dispersed inactivation reagent mixture would not last long in the IMx® instrument as the hydrogen peroxide component would evaporate under about 5 minutes and thus the mixture would not inactivate or would not detectably inactivate the amplified target nucleotide sequences in the next batch of samples placed in the IMx® instrument to be assayed. Further, even if the hydrogen peroxide has not evaporated, the aerolized inactivating reaction mixture would be in such small quantity compared to the next batch of samples to be assayed, that it would not inactivate or detectably inactivate the amplified nucleotide sequences in the next samples.

To avoid further contamination by any remaining LCR or PCR products that have not been inactivated in the above step, the IMx® instrument then automatically seals the entire reaction cell, including the top of the eppendorf tubes, with a strip of adhesive tape. It may not be necessary to seal the reaction cell as the inactivation is highly efficacious.

The operator can then open the front panel of the IMx® instrument and dispose of the used IMx® reaction cells.

All publications and patent applications mentioned in this Specification are herein incorporated by reference to the same extent as if each of them had been individually indicated to be incorporated by reference.

Although the foregoing invention has been described in some detail by way of illustration and examples for purposes of clarity and understanding, it will be obvious that the above methods, reagents, kits, and metal chelates, can be used in any situation where nucleotide sequences are to be eliminated. Further, various modifications and changes which are within the skill of those skilled in the art are considered to fall within the scope of the appended claims. Future technological advancements which allows for obvious changes in the basic invention herein are also within the claims.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 350 base pairs (B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:1:

```
GCCAGCCCCC  TGATGGGGGC  GACACTCCAC  CATGAATCAC  TCCCCTGTGA  GGAACTACTG    60
TCTTCACGCA  GAAAGCGTCT  AGCCATGGCG  TTAGTATGAG  TGTCGTGCAG  CCTCCAGGAC   120
CCCCCCTCCC  GGGAGAGCCA  TAGTGGTCTG  CGGAACCGGT  GAGTACACCG  GAATTGCCAG   180
GACGACCGGG  TCCTTTCTTG  GATCAACCCG  CTCAATGCCT  GGAGATTTGG  GCGTGCCCCC   240
GCAAGACTGC  TAGCCGAGTA  GTGTTGGGTC  GCGAAAGGCC  TTGTGGTACT  GCCTGATAGG   300
GTGCTTGCGA  GTGCCCCGGG  AGGTCTCGTA  GACCGTGCAC  CATGAGCACG               350
```

(2) INFORMATION FOR SEQ ID NO:2:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:2:

```
CACTCCACCA  TGAATCACTC  CCCT                                              24
```

(2) INFORMATION FOR SEQ ID NO:3:

(i) SEQUENCE CHARACTERISTICS:
(A) LENGTH: 27 base pairs
(B) TYPE: nucleic acid
(C) STRANDEDNESS: single
(D) TOPOLOGY: linear

(i i) MOLECULE TYPE: DNA (genomic)

(x i) SEQUENCE DESCRIPTION: SEQ ID NO:3:

```
AGTCTTGGGG  GGGCACGCCC  AAATCTC                                           27
```

I claim:

1. A method for chemically cleaving nucleotide sequences comprising the steps of exposing said nucleotide sequences to an oxidizing agent, a reducing agent, and a metal chelate complex having a formula selected from the group consisting of I, II and III:

I

II

III wherein "M" denotes a metal.

2. The method of claim 1, wherein M is a metal that catalyzes an oxidation-reduction reaction.

3. The method of claim 2, wherein M is a transition metal.

4. The method of claim 3, wherein M is selected from the group consisting of: nickel, copper, iron, zinc, ruthenium, rhodium, and cobalt.

5. The method of claim 1, wherein the oxidizing agent is selected from the group consisting of: peroxides and persulfates.

6. The method of claim 5, wherein the peroxides and persulfates are selected from the group consisting of: oxone, t-butyl hydroperoxide, peracetic acid, magnesium monoperoxyphthalate, sodium persulfate, and ammonium persulfate, and hydrogen peroxide.

7. The method of claim 6, wherein the oxidizing agent is hydrogen peroxide.

8. The method of claim 1, wherein the nucleotide sequences are selected from the group consisting of polymerase chain reaction products and ligase chain reaction products.

9. The method of claim 1, wherein the method chemically cleaves at least about 40% of the nucleotide sequences.

10. The method of claim 1, wherein for each mole of nucleotide sequence, there are between $1.8 \times 10^{-1}$ to $3.6 \times 10^5$ moles of metal chelate complex, and $2.4 \times 10$ to $9.6 \times 10^7$ moles of oxidizing agent.

11. The method of claim 10, wherein the metal chelate is about $1.8 \times 10^5$ moles, and the oxidizing agent is about $2.4 \times 10^7$ moles.

12. The method of claim 1, wherein the metal chelate complexes are selected from the group consisting of compounds VI and VII of the following formulae:

(ClO$_4$)$_2$$^-$

VI

(ClO$_4$)$_2$$^-$

VII

13. The method of claim 1, wherein a counterion for the metal chelate complexes is either a monovalent or divalent anion.

14. The method of claim 13, wherein the counterion is selected from the group consisting of: chloride, bromide, sulfate, tetraflouoroborate, tetraphenylborate, hexafluorophosphate, nitrate, and perchlorate.

15. A method of chemically cleaving nucleotide sequences, including amplified target nucleotide sequences, comprising the steps of:
(a) amplifying target nucleotide sequences;
(b) detecting the amplified target nucleotide sequences; and
(c) chemically cleaving the nucleotide sequences, including the amplified target nucleotide sequences, by exposing them to an oxidizing agent, a reducing agent, and a metal chelate complex of chemical formulae selected from the group consisting of I, II and III:

I

II

III wherein "M" denotes a metal.

16. The method of claim 15, wherein the oxidizing agent is selected from the group consisting of: peroxides and persulfates.

17. The method of claim 16, wherein the peroxides and persulfates are selected from the group consisting of: oxone, t-butyl hydroperoxide, peracetic acid, magnesium monoperoxyphthalate, sodium persulfate, and ammonium persulfate, and hydrogen peroxide.

18. The method of claim 17, wherein the oxidizing agent is hydrogen peroxide.

19. The method of claim 15, wherein M is a metal that catalyzes an oxidation-reduction reaction.

20. The method of claim 19, wherein M is a transition metal selected from the group consisting of: nickel, copper, iron, zinc, ruthenium, rhodium, and cobalt.

21. The method of claim 15, wherein the nucleotide sequences are selected from the group consisting of polymerase chain reaction products and ligase chain reaction products.

22. A metal chelate complex selected from the group consisting of I, II and III with the following formulae:

I wherein "M" denotes a metal.

23. The metal chelate complex of claim 22, wherein a counterion for the metal chelate complex is selected from the group consisting of monovalent and divalent anions.

24. The metal chelate complex of claim 23, wherein the metal chelate complex when coupled to the counterion, is of a formula selected from the group consisting of formulae VI and VII:

25. The metal chelate complex of claim 22, wherein M is a metal that catalyzes an oxidation-reduction reaction.

26. The metal chelate complex of claim 25, wherein M is a transition metal selected from the group consisting of: nickel, copper, iron, zinc, ruthenium, rhodium, and cobalt.

27. A kit for chemically cleaving nucleotide sequences comprising:

a) a container containing a metal chelate complex having chemical formulae selected from the group consisting of I, II, and III:

wherein "M" denotes a metal; and b) another container containing an oxidizing agent.

28. The kit of claim 27, wherein M is a transition metal that catalyzes an oxidation-reduction reaction.

29. The kit of claim 28, wherein M is selected from the group consisting of: nickel, copper, iron, zinc, ruthenium, rhodium, and cobalt.

30. The kit of claim 29, wherein the metal chelate complexes are selected from the group consisting of compounds VI and VII of the following formulae:

31. The kit of claim 27, wherein the oxidizing agent is selected from the group consisting of: peroxides and persulfates.

32. The kit of claim 31, wherein the peroxides and persulfates are selected from the group consisting of: oxone, t-butyl hydroperoxide, peracetic acid, magnesium monoperoxyphthalate, sodium persulfate, ammonium persulfate, and hydrogen peroxide.

33. The kit of claim 31, wherein the oxidizing agent is hydrogen peroxide.

* * * * *